US008318205B2

(12) United States Patent
Kataoka et al.

(10) Patent No.: US 8,318,205 B2
(45) Date of Patent: *Nov. 27, 2012

(54) POLYETHYLENE GLYCOL/POLYCATION BLOCK COPOLYMERS

(75) Inventors: Kazunori Kataoka, Tokyo (JP); Naoki Kanayama, Wako (JP); Keiji Itaka, Tokyo (JP); Shigeto Fukushima, Narashino (JP); Atsushi Harada, Sakai (JP)

(73) Assignee: The University of Tokyo, Tokyo (JP)

( * ) Notice: Subject to any disclaimer, the term of this patent is extended or adjusted under 35 U.S.C. 154(b) by 381 days.

This patent is subject to a terminal disclaimer.

(21) Appl. No.: 12/656,307

(22) Filed: Jan. 25, 2010

(65) Prior Publication Data

US 2010/0137512 A1    Jun. 3, 2010

Related U.S. Application Data

(63) Continuation of application No. 10/556,058, filed as application No. PCT/JP2004/006488 on May 7, 2004, now Pat. No. 7,780,957.

(30) Foreign Application Priority Data

May 8, 2003    (JP) .................................. 2003-130520
Sep. 8, 2003    (JP) .................................. 2003-315858

(51) Int. Cl.
*A61K 9/14*    (2006.01)
(52) U.S. Cl. ...................................................... 424/486
(58) Field of Classification Search ........................ None
See application file for complete search history.

(56) References Cited

U.S. PATENT DOCUMENTS

| 3,243,399 A | 3/1966 | Knapp et al. |
| 7,138,490 B2 | 11/2006 | Nakanishi et al. |
| 2003/0017972 A1 | 1/2003 | Pun et al. |

FOREIGN PATENT DOCUMENTS

| CA | 2 377 211 | 1/2001 |
| JP | 5-117385 | 5/1993 |
| JP | 6-206832 | 7/1994 |
| JP | 2001-120268 | 5/2001 |
| JP | 2001-146556 | 5/2001 |
| JP | 2001-226294 | 8/2001 |
| WO | 00/71602 | 11/2000 |
| WO | 2003/000771 | 3/2003 |

OTHER PUBLICATIONS

International Search Report issued Aug. 10, 2004 in International (PCT) Application No. PCT/JP2004/006488.
Machine English Translation of JP 2001146556.
Eberhard W. Neuse et al., "Water-soluble polyamides as potential drug carriers, II", Die Angewandte Makromolekulare Chemie, 181, pp. 153-170, 1990.
Eberhard W. Neuse et al., "Water-soluble polyamides as potential drug carriers", Die Angewandte Makromolekulare Chemie, 192 pp. 35-50, 1991.
Canadian Office Action issued Sep. 16, 2010 in counterpart Canadian Application No. 2,524,907.

*Primary Examiner* — Paul Dickinson
(74) *Attorney, Agent, or Firm* — Wenderoth, Lind & Ponack, L.L.P.

(57) ABSTRACT

The invention provides block copolymers formed of poly (ethylene glycol) segments and poly(amino acid derivative) segments having side chains of at least one kind of specific amine residue. The invention also provides polyion complexes of such copolymers with polynucleotides and the like. These block copolymers are useful as carriers for in vivo delivery of active substances such as DNA.

10 Claims, 7 Drawing Sheets

POLYETHYLENE GLYCOL/POLYCATION BLOCK COPOLYMERS

CROSS REFERENCE

This application is a Continuation application of Ser. No. 10/556,058, filed Nov. 8, 2005 now U.S. Pat. No. 7,780,957, which is 371 application of PCT/JP2004/006488, filed May 7, 2004.

TECHNICAL FIELD

This invention relates to block copolymers having polyethylene glycol structural portion as a hydrophilic segment and polyamino acid structural portion having amine residue side chains of various structures as a cationic segment; and also to polyion complexes of the copolymers with nucleic acid or anionic proteins.

BACKGROUND ART

A polyethylene glycol/polycation block copolymer represented by polyethylene glycol-block-poly(L-lysine) which is a cationic block copolymer spontaneously forms a spherical micelle with an anionic macromolecule, due to the electrostatic interaction acting between the two in water as a driving power. This particle has a diameter of several tens nanometers and a core-shell structure, the core (or inner nucleus) being formed of polyion complex of cation and anion, and the shell (or outer shell) being a polyethylene glycol (which may be hereafter abbreviated as "PEG") layer. The particle is referred to as polyion complex (PIC) micelle (see, e.g., Non-patent Reference 1 which is identified later, like other references). Thus, PIC micelles can hold anionic macromolecules in inner nuclei and are therefore expected to be capable of avoiding in vivo foreign matter recognizing mechanism due to such particle diameter as several tens nanometers and the core-shell structure. Accordingly, presently their application as a carrier (vector) of DNA which is a natural anionic macromolecule is under investigation. Although priority in developing gene vectors using such cationic block copolymers is thus clear, due to limitations on their synthesis and for other reasons, cationic block copolymers which are currently investigated do not extend beyond PEG-block-poly(L-lysine), PEG-block-poly(dimethylaminoethyl methacrylate) (see, e.g., Patent Reference 1) and PEG-block-polyethylenimine.

These PIC micelles are considerably stable under physiological conditions in general, but is actual use their stability under physiological conditions is occasionally insufficient, as exemplified by dissociation of PIC micelles under dilution after administration by intravenous injection or their interaction with serum proteins. This necessitates modification of properties of PIC micelles so that they would not dissociate but exist stably for a fixed period, until they arrive at the intended site with certainty or after their arrival. As a means to so modify properties of PIC micelles, for example, it has been proposed to improve stability of PIC micelles by introducing mercaptoalkyl groups into amino groups in a fixed proportion of L-lysine units in poly(L-lysine) segments in said PEG-block-poly-(L-lysine) to form disulfide bonds between said groups (see, e.g., Patent Reference 2).

Also as a new type, a copolymer formed by ester-amide exchange of benzyl groups in PEG-block-poly(β-benzylaspartate) with, for example, N,N-dimethylethylenediamine or the like (see, e.g. Non-patent Reference 2).

The function of polycation blocks in the micelles formed of polycation and DNA is mainly to serve as the electrostatic interaction site with the DNA, while in principle still other functions can be imparted. As one of such functions, there is proton sponge effect. Proton sponge effect refers to a phenomenon: when a polyamine of low degree of protonation is incorporated in endosomes, it absorbs hydrogen ions supplied into the endosomes by V-type ATPase one after another to prevent pH drops within the endosomes and in consequence to cause expansion of the endosomes with water infiltration accompanying rise in osmotic pressure in the endosomes, which eventually leads to destruction of the endosomes. It is expected that transfer of DNA to cytoplasm is promoted and the gene expression effectiveness is increased by this effect. This effect is seen in cations having buffer ability and, therefore, use of cations of low pKa is necessary.

On the other hand, gene expression effectiveness is considered to be affected also by stability of PIC micelles, condensed state of enclosed DNA and the like, and such factors also are presumed to be dependent on properties of individual polycation. As aforesaid, however, heretofore the kinds of studied polycation are limited and there has been no concept of simultaneous introduction of two or more kinds of polycations to allot them different functions. Under the circumstances, it was very difficult to control these factors.

LIST OF CITED REFERENCES

Patent Reference 1: WO98/46655 (cf. pp. 20-21, Examples 10 and 11)
Patent Reference 2: JP2001-146556A
Non-patent Reference 1: Harada and Kataoka, *Macromolecules*, 1995, 28, 5294-5299
Non-patent Reference 2: *Polymer Preprints*, Japan, Vol. 51, No. 5 (2002)

DISCLOSURE OF THE INVENTION

For example, PEG-block-polycation as described in above Patent Reference 2 and Non-patent Reference 2 form polyion complex micelles (PIC micelles) stably enclosing DNA, but provision of PIC micelles exhibiting still new properties is called for, in consideration of the versatility in environments of target living bodies to which physiologically active substances such as DNA are to be delivered or the optimum release rate of said physiologically active substance from PIC micelles under individual environment.

We have discovered that a PEG-block-polycation copolymer whose polycation segment has bulky side chains of low pKa can enclose DNAs in substantially free state, as contrasted with those copolymers described in Non-patent Reference 2 in which PIC micelles enclose DNAs in considerably condensed state; and also that such DNAs which are enclosed in free state are released at a significantly slower rate than those enclosed in condensed state, when, for example, they come to contact with the target cells to which they are to be delivered, under physiological conditions.

We have furthermore discovered: when the polycation contains both primary amine and secondary or tertiary amine, the primary amine chiefly participates in formation of associated particle with DNA, while the secondary or tertiary amine scarcely participates. Further concentratively pursuing the investigations, we have completed the present invention.

Thus, the present invention relates to: (1) a polyethylene glycol/polycation block copolymer characterized by having segment A formed of polyethylene glycol or a derivative thereof and segment B formed of polyamino acid, a derivative thereof or a salt of the foregoing, the segment B containing bulky amines of pKa value not higher than 7.4 or containing both primary amine and secondary amine, tertiary amine or quaternary ammonium salt;

as a specific embodiment, (2) the copolymer as described in (1) above, in which the structure of the block copolymer is one represented by a general formula (I) or (II) or a salt thereof, (in which R¹ stands for hydrogen, or a substituted or unsubstituted, straight or branched chain $C_{1-12}$ alkyl, $L^1$ and $L^2$ stand for linkers, $R^2$ stands for methylene or ethylene, $R^3$ stands for hydrogen, protective group, hydrophobic group or polymerizable group, $R^4$ is either same as $R^5$ or an initiator residue, $R^5$s each independently stands for hydroxyl, oxybenzyl or $-NH-(CH_2)_a-X$ group, wherein X each independently stands for a bulky amine compound residue having a pKa value not higher than 7.4 or an amine compound residue containing one, two or more members of the group consisting of primary, secondary and tertiary amines and quaternary ammonium salt, or a residue of a compound which is not amine, a is an integer of 1-5, m is an integer of 5-20,000, n is an integer of 2-5,000 and x is an integer of 0-5,000, with a proviso that x is not greater than n);

as a specific embodiment, (3) the copolymer as described in (1) above, in which the structure of the block copolymer is one represented by a general formula (III) or (IV) or a salt thereof, (in which R¹ stands for hydrogen, or a substituted or unsubstituted, straight or branched chain $C_{1-12}$ alkyl, $L^1$ and $L^2$ stand for linkers, $R^2$ stands for methylene or ethylene, $R^3$ stands for hydrogen, protective group, hydrophobic group or polymerizable group, $R^4$ is either same as $R^5$ or an initiator residue, $R^5$s each independently stands for hydroxyl, oxybenzyl or $-NH-(CH_2)_a-X$ group, wherein X each independently stands for a bulky amine compound residue having a pKa value not higher than 7.4 or an amine compound residue containing one, two or more members of the group consisting of primary, secondary and tertiary amines and quaternary ammonium salt, or a residue of a compound which is not amine, a is an integer of 1-5, $R^6$ each independently stands for hydrogen or a protective group, wherein the protective group is Z, Boc, acetyl, trifluoroacetyl or the like which are customarily used as protective groups of amino, m is an integer of 5-20,000, n is an integer 2-5,000, y is an integer of 0-4,999 and z is an integer of 1-4,999, with the proviso that z is less than n and y+z is not more than n);

as a still more specific embodiment, (4) a copolymer as described in (2) or (3) above, in which $R^1$ is methyl;

as a more specific embodiment, (5) a copolymer as described in (2) or (3), in which $R^1$ stands for substituted straight or branched chain $C_{1-12}$ alkyl, wherein the substituent is acetalized formyl, cyano, formyl, carboxyl, amino, $C_{1-6}$ alkoxycarbonyl, $C_{2-7}$ acylamide, same or different tri-$C_{1-6}$ alkylsiloxy, siloxy or silylamino;

as a further specific embodiment, (6) a copolymer as described in any one of (2)-(5) above, in which $L^1$ is $-(CH_2)_b-NH-$, b being an integer of 1-5;

as a still more specific embodiment, (7) a copolymer as described in (2); and further in any one of (3)-(5) above, in which $L^2$ is $-(CH_2)_c-CO-$, c being an integer of 1-5;

as a still more specific embodiment, (8) a copolymer as described in any one of (2)-(7) above, in which $R^2$ is methylene;

as a still more specific embodiment, (9) a copolymer as described in any one of (2)-(8) above, in which X is a group represented by the following Groups A, B, C, D or E, Group A:

Group B:

Group C:

Group D:

—N(CH₃)₂ or

Group E:

(in the above formulae, $X^2$ stands for hydrogen or $C_{1-6}$ alkyl, $X^3$ stands for amino $C_{1-6}$ alkyl, $R^7$ stands for hydrogen or methyl, d stands for an integer of 1-5, e stands for an integer of 1-5, f stands for an integer of 0-15, $R^8$ stands for a protective group, wherein the protective group is Z, Boc, acetyl, trifluoroacetyl or the like which are customarily used as protective groups of amino, and g stands for an integer of 0-15);

as a still more specific embodiment, (10) a copolymer as described in any one of (2)-(9) above, in which $R^3$ is acetyl, acryloyl or methacryloyl;

as a still more specific embodiment, (11) a copolymer as described in any one of (2)-(10) above, in which $R^4$ is —NH—$R^9$, $R^9$ standing for unsubstituted or substituted, straight or branched chain $C_{1-20}$ alkyl;

as another embodiment, (12) a polyion complex comprising a copolymer as described in any one of (1)-(11) above and nucleic acid or anionic protein; and as a more specific embodiment, (13) a polyion complex as described in (12) above, which is in the form of a polymer micelle carrying nucleic acid or anionic protein in its core portion with the shell portion composed mainly of polyethylene glycol segment.

EFFECT OF THE INVENTION

This invention enables to control those factors which affect gene transfer effectivity such as the condensed state of genes in PIC micelles, release rate of the genes from the micelles, proton-sponge effect, micelle stability and the like. The invention enables provision of PIC micelles having higher gene transfer effectivity. The invention also enables provision of more useful non-viral gene vectors.

BEST EMBODIMENTS FOR WORKING THE INVENTION

In the general formulae (I), (II), (III) or (IV), $R^1$ stands for hydrogen or unsubstituted or substituted straight or branched chain $C_{1-12}$ alkyl. As $C_{1-12}$ alkyl, methyl, ethyl, n-propyl, isopropyl, n-butyl, sec-butyl, tert-butyl, n-pentyl, n-hexyl, decyl, undecyl and the like can be named. When the alkyl groups are substituted, as the substituent acetatalized formyl, cyano, formyl, carboxyl, amino, $C_{1-6}$ alkoxycarbonyl, $C_{2-7}$ acylamide, same or different tri-$C_{1-6}$ alkylsiloxy, siloxy or silylamino can be named. Where the substituent is acetalized formyl, it can be hydrolyzed under mildly acidic conditions to be converted to formyl (—CHO: or aldehyde) which is another substituent. Such formyl, carboxyl or amino group can be present, for example, at the shell portion of polyion complex micelle of a copolymer following the present invention and nucleic acid or anionic proteins and can be utilized for covalently bonding with the micelles antibodies or fragments having the specific bindability thereof (F(ab')2, F(ab), and the like) and proteins which are capable of imparting to the micelles other functionality or target directivity, via these groups. PEG segments having such functional groups at one end can be conveniently formed by, for example, the preparation processes of PEG segments of block copolymers as described in WO96/32434, WO96/33233 and WO97/06202.

Thus formed PEG segment portion and poly (amino acid or a derivative thereof) segment portion can take any form of linkage according to the method used for preparing the copolymers of the general formula (I), (II), (III) or (IV) and any linker may be used for the linkage so long as the objects of the present invention are achieved.

The preparation method is subject to no special limitation. For example, a method can be used in which a PEG derivative having an amino group at one end is used to synthesize a block copolymer through polymerization starting from the amino terminal, of N-carboxylic anhydride (NCA) of protective amino acid such as β-benzyl-L-aspartate, Nε-Z-L-lysine or the like, and then the side chains are converted. In this case, the formed copolymer has a structure of the general formula (I) or (III) and the linker $L^1$ takes a structure derived from the terminal structure of the PEG derivative used, which preferably is —$(CH_2)_b$—NH—, b being an integer of 1-5.

A copolymer of the present invention can be prepared also by a method comprising synthesizing a poly(amino acid or a derivative thereof) segment potion and then linking it with a PEG segment portion. In that case, the copolymer may have a same structure as that of the product of above-described method, or may have a structure of the general formula (II) or (IV). The linker $L^2$ is not critical, but preferably —$(CH_2)_c$—CO—, c being an integer of 1-5.

In the general formula (I), (II), (III) or (IV), $R^5$ each independently stands for hydroxyl, oxybenzyl, —NH—$(CH_2)_a$—X, it being preferred that most of $R^5$s (generally at least 85%, preferably at least 95%, in particular, at least 98%, inter alia, 100%) are —NH—$(CH_2)_a$—X. Again, $R^6$ in the general formula (III) or (IV) can each independently stand for hydrogen or a protective group, it being preferred that most of $R^6$s are hydrogen atoms. Here the protective group means those normally used as protective groups of amino, such as Z group, Boc group, acetyl group, trifluoroacetyl group and the like.

X is subject to no particular limitation so long as the copolymers satisfy the conditions of the present invention (or meet the objects of the present invention). It is selected from residues classified into five groups: i.e., Group A; bulky amine compound residues having a pKa value not more than 7.4

Group B; amine compound residues containing both primary amine and secondary amine, tertiary amine or quaternary ammonium salt Group C; amine compound residues containing primary amine only —$(CH_2)_f$—$NH_2$ Group D; amine compound residues containing secondary amine, tertiary amine or quaternary ammonium salt only, which are not included in Group A —$(NR^7(CH_2)_d)_e$—$NHR^8$,

—$N(CH_3)_2$ or

—$N(CH_2CH_3)_2$ and

Group E; residues of compounds other than amine

Those copolymers represented by the general formula (I) or (II) may contain any one residue only selected from the residues of Groups A and B; where they contain a residue of Group C, they must concurrently contain at least one residue selected from the residues of Groups A and D; and where they contain a residue of Group D, they must concurrently contain at least one residue selected from the residues of Groups B and C. Group E residue or residues can be contained in the copolymers to vary physical properties of the copolymers, but in that case the structure of the copolymers except the Group E residue portions must satisfy the above requirements. The copolymers of the general formula (III) or (IV) may contain any one residue only which is selected from the residues of Groups A, B and D, where at least one of $R^6$s is hydrogen atom. Requirements for the copolymers containing Group C residue(s) and Group (E) residue(s) are same as above.

Examples of preferred residues in each Group are shown referring to the formulae. In the formulae, $X^2$ in Group A is hydrogen or $C_{1-6}$ alkyl; in Group B, $X^3$ is amino $C_{1-6}$ alkyl, $R^7$ is hydrogen or methyl, and d and e are each an integer of 1-5; in Group C, f is an integer of 0-15; in Group D, d and e each is an integer of 1-5 and $R^8$ is a protective group such as Z group, Boc group, acetyl group, trifluoroacetyl group and the like; and in Group E, g can be an integer of 0-15.

As a method for introducing these residues into side chains of polyamino acid structure, particularly when the latter is polyaspartic acid structure, the introduction can be conveniently carried out by transesterification from ester to amide by aminolysis of poly-(β-benzyl-L-aspartate) portion as described in, for example, JP 2,777,530. As another method, the benzyl ester is converted to polyaspartic acid or polyglutamic acid by catalystic reduction or hydrolysis using an acid or alkali, and thereafter a compound having these residues is linked thereto using a condensing agent or the like.

These cationic side chains may be in the form of salt. In that case, as the pair ions to form the salt, $Cl^-$, $Br^-$, $I^-$, $(\frac{1}{2}SO_4)^-$, $NO_3^-$, $(\frac{1}{2}CO_3)^-$, $(\frac{1}{3}PO_4)^-$, $CH_3COO^-$, $CF_3COO^-$, $CH_3SO_3^-$, $CF_3SO_3^-$ and the like can be named.

$R^2$ in the general formula (I), (II), (III) or (IV) stands for methylene or ethylene, and where $R^2$ is methylene, the copolymer corresponds to poly(aspartic acid derivative), and where $R^2$ is ethylene, corresponds to poly(glutamic acid derivative). When $R^2$ in these general formulae stands for both methylene and ethylene groups, the recurring units of aspartic acid derivative and glutamic acid derivative may be present forming blocks respectively, or may be present at random.

R³ in the general formula (I) or (III) stands for hydrogen, a protective group, hydrophobic group or polymerizable group. As the protective group, $C_{1-6}$ alkylcarbonyl, preferably acetyl, can be named. As the hydrophobic group, derivatives of benzene, naphthalene, anthracene, pyrene and the like can be named. As the polymerizable groups, methacryloyl and acryloyl can be named, and when copolymers of the general formula (I) or (III) have such polymerizable groups, they can be used as those which are generally referred to as macromers. For example, after formation of PIC micelles, the copolymers can be crosslinked via these polymerizable groups, using other comonomer(s) where necessary.

As the means to introduce these protective groups, hydrophobic groups or polymerizable groups into terminals of the copolymers, those used in ordinary syntheses such as method of using acid halide, method of using acid anhydride, method of using active ester, and the like can be named.

R⁴ in the general formula (II) or (IV) can be hydroxyl, oxybenzyl, or —NH—(CH₂)ₐ—X, similar to R⁵. When the block copolymer is prepared by a method comprising synthesizing a poly(amino acid or a derivative thereof) segment by polymerizing NCA of protective amino acid using a low molecular weight initiator, and then linking it with a PEG segment, R⁴ may take a structure derived from the initiator used, i.e., —NH—R⁹, R⁹ being unsubstituted or substituted straight or branched chain $C_{1-20}$ alkyl.

Chain lengths of the PEG segment and poly(amino acid or a derivative thereof) segment are specified by m and n, respectively, m being an integer of 5-20,000, preferably 10-5,000, inter alia, 40-500, and n being 2-5,000, preferably 5-1,000, inter alia, 10-200. However, when the copolymers of the general formula (I), (II), (III) or (IV) are those forming PIC micelles with nucleic acid or anionic proteins, the chain lengths are not limited. Therefore, while the terms, polyethylene glycol and polycation, are used in this specification for convenience, "poly" therein signifies the concept encompassing those customarily classified under "oligo".

Again, x, y and z which specify the constitution ratio of poly-(amino acid or a derivative thereof) segment are, respectively, an integer of 0-5,000 (provided it is not greater than n), an integer of 0-4,999, and an integer of 1-4,999 (provided that z is smaller than n and y+z is not greater than n). Preferably, z lies within a range of 10–n–10. Each constituent component may be distributed at random or as blocks.

Those copolymers represented by the general formula (I), (II), (III) or (IV) can conveniently form PIC micelles having polyion complex of polycation portion of said copolymer and, for example, nucleic acid as the core and the PEG layer as the shell, when stirred in an aqueous medium (which may contain water-miscible organic solvent) at room temperature, with nucleic acid, e.g., genes encoding other genes useful for known gene therapy or therapeutically necessary proteins; DNA fragments such as plasmids, RNA fragments, antisense DNA and the like which contain such genes; or anionic proteins (or peptides) (in particular, those anionically chargeable at physiological pH). According to the present invention, such PIC or PIC micelles themselves also are provided.

Hereinafter the invention is more specifically explained, referring to specific examples, it being understood that the examples are given exclusively for the sake of explanation.

EXAMPLE 1

Synthesis of Polyethylene Glycol/Poly(β-Benzyl-L-Aspartate)-Ac Block Copolymer

Polyethylene glycol (MeO-PEG-NH₂) with methoxy at one end and aminopropyl at the other end, having an average molecular weight of 12,000 was dissolved in methylene chloride, and to which a solution of β-benzyl-L-aspartate-N-carboxylic anhydride (BLA-NCA) in a mixed solvent of N,N-dimethylformamide (DMF) and methylene chloride was added. Allowing the components to react at 40° C. for two days, polyethylene glycol-poly(β-benzyl-L-aspartate) block copolymer (MeO-PEG-PBLA) was obtained. Further the N-terminal was acetylated with acetic anhydride, to provide MeO-PEG-PBLA-Ac. The average molecular weight of the PBLA portion was 14,000 and the degree of polymerization was 68, as determined by ¹H-NMR analysis.

EXAMPLE 2

Preparation of Polyethylene Glycol/Polycation Block Copolymer by Aminolysis with Morpholinopropylamine MeO-PEG-PBLA-Ac as obtained in Example 1 was dissolved in benzene and lyophilized. Morpholinopropylamine was distilled under reduced pressure with calcium hydride serving as a desiccant.

MeO-PEG-PBLA-Ac was dissolved in dry DMF, to which 10 (mol) eq. of morpholinopropylamine to the PBLA unit was added and stirred for 24 hours at 40° C. in argon atmosphere. After the 24 hours, the reaction solution was added dropwisely into 10% aqueous acetic acid solution, followed by dialysis against 0.01N-aqueous hydrochloric acid solution with a dialyzer with MWCO=3,500. Evaporating and lyophilizing the liquid inside of the dialyzer, the object product (MeO-PEG-MOPA) was obtained as a white solid. The structure of the polymer was confirmed by means of ¹H-NMR.

In consequence, the peaks attributable to the benzyl groups in the MeO-PEG-PBLA-Ac completely disappeared and newly proton signals originated from the amide formation were confirmed. From integral values, approximately quantitative progress in aminolysis of polymer side chains was confirmed.

EXAMPLE 3

Preparation of Polyethylene Glycol/Polycation Block Copolymer

[wherein R

]
by aminolysis with diethylenetriamine

MeO-PEG-PBLA-Ac as obtained in Example 1 was dissolved in benzene and lyophilized. Diethylenetriamine was distilled under reduced pressure with calcium hydride serving as a desiccant.

MeO-PEG-PBLA-Ac was dissolved in dry DMF, to which 50 (mol) eq. of diethylenetriamine to the PBLA unit was added and stirred for 24 hours at 40° C. in argon atmosphere. After the 24 hours, the reaction solution was added dropwisely into 10% aqueous acetic acid solution, followed by dialysis against 0.01N-aqueous hydrochloric acid solution with a dialyzer with MWCO=3,500. Lyophilizing the liquid inside the dialyzer, the object product (MEO-PEG-DET) was obtained as a white solid.

The structure of the produced polymer was confirmed by $^1$H-NMR.

In consequence, the peaks attributable to the benzyl groups in the MeO-PEG-PBLA-Ac completely disappeared and newly proton signals originated from the amide formation were confirmed. From integral values, approximately quantitative progress in aminolysis of polymer side chains was confirmed.

COMPARATIVE EXAMPLE 1

Preparation of Polyethylene Glycol/Polycation Block Copolymer

[wherein R=

]
by aminolysis with N,N-dimethylpropylamine

MeO-PEG-PBLA-Ac as obtained in Example 1 was dissolved in benzene and lyophilized. N,N-dimethylpropylamine was distilled under reduced pressure with calcium hydride serving as a desiccant.

MeO-PEG-PBLA-Ac was dissolved in dry DMF, to which 10 (mol) eq. of N,N-dimethylpropylamine to the PBLA unit was added and stirred for 24 hours at 40° C. in argon atmosphere. After the 24 hours, the reaction solution was added dropwisely into 10% aqueous acetic acid solution, followed by dialysis against 0.01N-aqueous hydrochloric acid solution with a dialyzer with MWCO=3,500. Evaporating and lyophilizing the liquid inside the dialyzer, the object product (MEO-PEG-DMAPA) was obtained as a white solid.

The structure of the produced polymer was confirmed by $^1$H-NMR.

In consequence, the peaks attributable to the benzyl groups in the MeO-PEG-PBLA-Ac completely disappeared and newly proton signals originated from the amide formation were confirmed. From integral values, approximately quantitative progress in aminolysis of polymer side chains was confirmed.

COMPARATIVE EXAMPLE 2

Preparation of Polyethylene Glycol/Polycation Block Copolymer

[wherein R=

]
by aminolysis with diaminopropane

MeO-PEG-PBLA-Ac as obtained in Example 1 was dissolved in benzene and lyophilized. Diaminopropane was distilled under reduced pressure with calcium hydride serving as a desiccant.

MeO-PEG-PBLA-Ac was dissolved in dry DMF, to which 50 (mol) eq. of diaminopropane to the PBLA unit was added and stirred for 24 hours at 40° C. in argon atmosphere. After the 24 hours, the reaction solution was added dropwisely into 10% aqueous acetic acid solution, followed by dialysis against 0.01N-aqueous hydrochloric acid solution with a dialyzer with MWCO=3,500. Evaporating and lyophilizing the liquid inside the dialyzer, the object product (MEO-PEG-DAP) was obtained as a white solid.

The structure of the produced polymer was confirmed by $^1$H-NMR.

In consequence, the peaks attributable to the benzyl groups in the MeO-PEG-PBLA-Ac completely disappeared and newly proton signals originated from the amide formation were confirmed. From integral values, approximately quantitative progress in aminolysis of polymer side chains was confirmed.

EXAMPLE 4

Formulation of PIC Micelles of Block Copolymer and Plasmid DNA

Plasmid DNA encoding luciferase (p-DNA, pGL3-Luc) was purified with Maxi kit of Quiagen GmbH and formulated into a solution at a concentration of 50 μg/ml with tris-hydrochloric acid buffer (10 mM, pH=7.4). Solutions of the copolymers as prepared in Example 2, Example 3, Comparative Example 1 and Comparative Example 2 (tris-hydrochloric acid buffer (10 mM, pH=7.4)) were each blended with the p-DNA solution to satisfy the N/P ratio each. The solutions were let stand an overnight in a dark place at room temperature. The solutions were transparent and formation of no aggregate or precipitate was observed. Here "N/P ratio" refers to "concentration of cation residues in the tested block copolymer" over "concentration of phosphoric acid group in p-DNA", while for the MeO-PEG-DET as prepared in Example 3 alone, it was calculated from the concentration of primary amino group only.

EXAMPLE 5

Characterization by Electrophoresis

A 0.9 wt % agarose gel was prepared and electrophoresis was conducted at p-DNA concentration of 0.17 μg/lane and using as the migration buffer tris-hydrochloric acid buffer (3.3 mM, pH=7.4) under the conditions of applied voltage of 50V and migration time of 2 hours. Thereafter staining was conducted with ethidium bromide solution (0.5 mg/L) for an hour.

Figure 1:
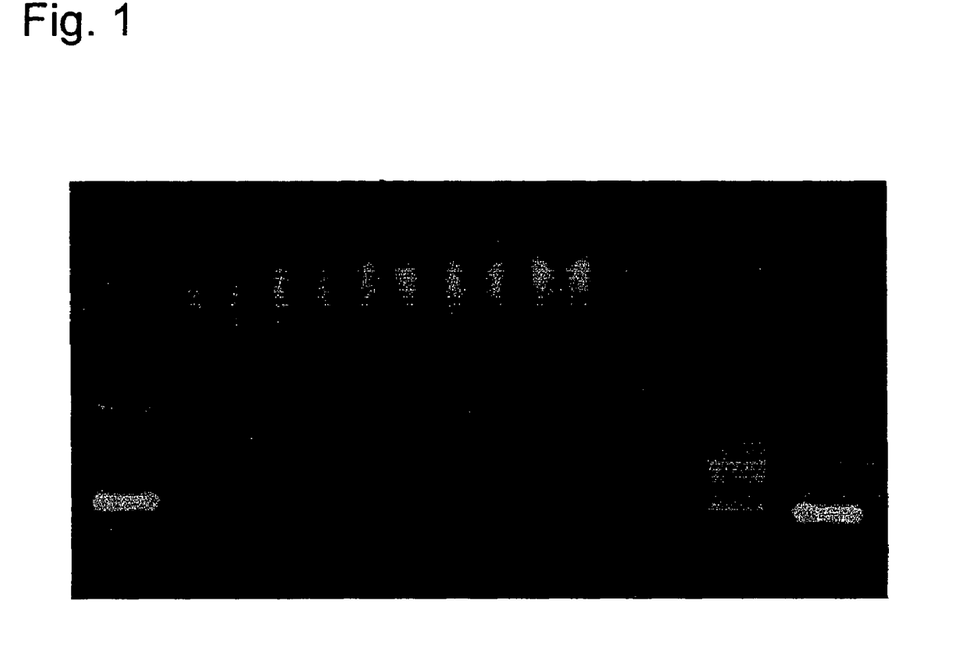
FIG. 1 is a photograph in place of a drawing, showing the result of electrophoreses of solutions of MeO-PEG-MOPA and p-DNA blended at various N/P ratios (N/P ratio: 0, 10, 5, 4, 3, 2, 1, 0, respectively, from the left). (Here N/P=0 signifies the lane in which p-DNA only is migrated.)
Figure 2:
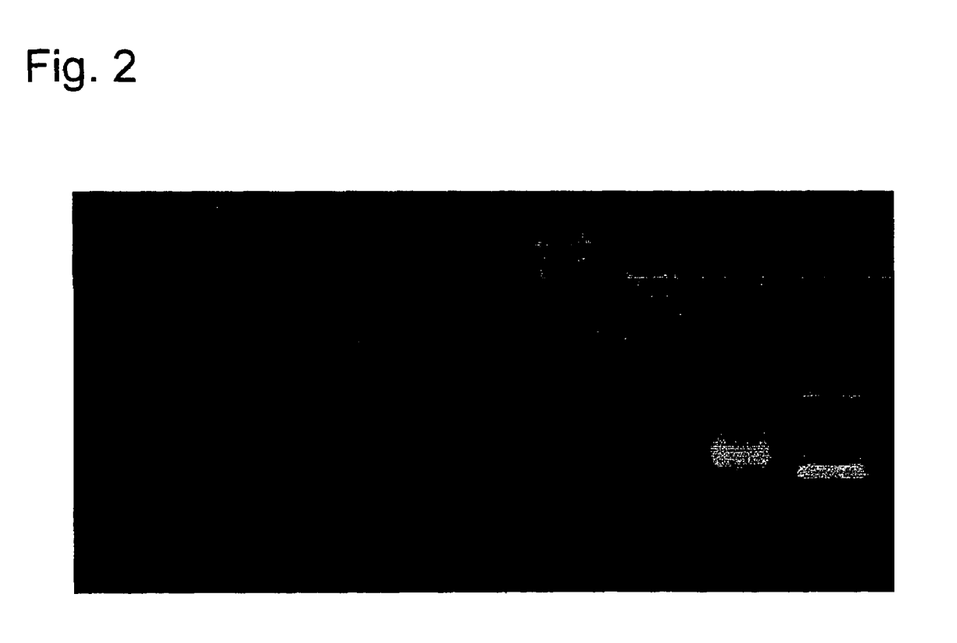
FIG. 2 is a photograph in place of a drawing showing the result of electrophoreses of solutions of MeO-PEG-DET and p-DNA blended at various N/P ratios (N/P ratio: 10, 5, 3, 2, 1, 0.5, 0.25, 0, respectively, from the left). (Here N/P=0 signifies the lane in which p-DNA only is migrated.)

FIG. 1 shows the result with MeO-PEG-MOPA and p-DNA mixed solution and FIG. 2, the result with MeO-PEG-DET and p-DNA mixed solution. In both, at the N/P ratio>1, the band attributable to free DNA disappeared, suggesting formation of PIC micelles. Also in consideration of the given definition of the N/P ratio, it was suggested that the primary amine in the block copolymers mainly participated in the formation of the associated particles with MeO-PEG-DET and secondary amine scarcely participated. In the associated particles the secondary amine remained in the system in deprotonated state, which could be interpreted as retaining buffer ability.

EXAMPLE 6

Characterization of Dynamic Light Scattering Method (DLS)

The particle diameter measurements were conducted by dynamic light scattering. The results were as shown in FIGS.

Figure 3:
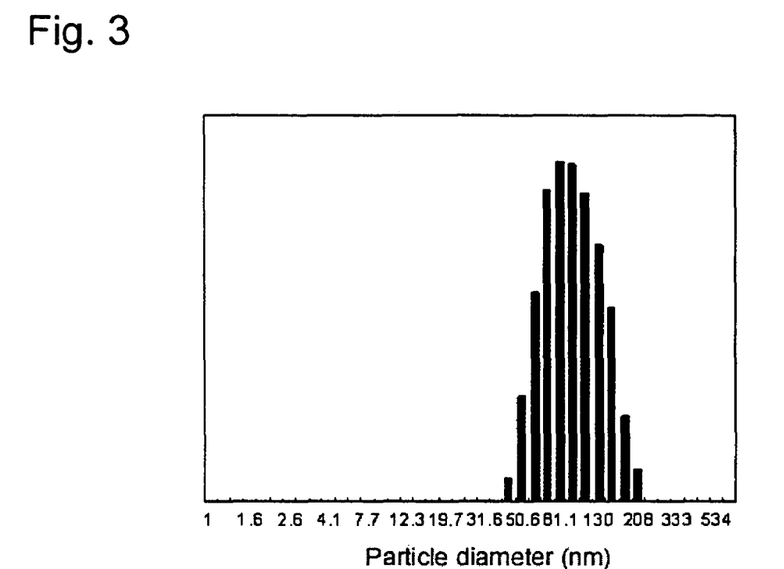
FIG. 3 is a graph showing particle size distribution of associated particles formed of MeO-PEG-MOPA and p-DNA, as measured by means of dynamic light scatting (DLS).
Figure 4:
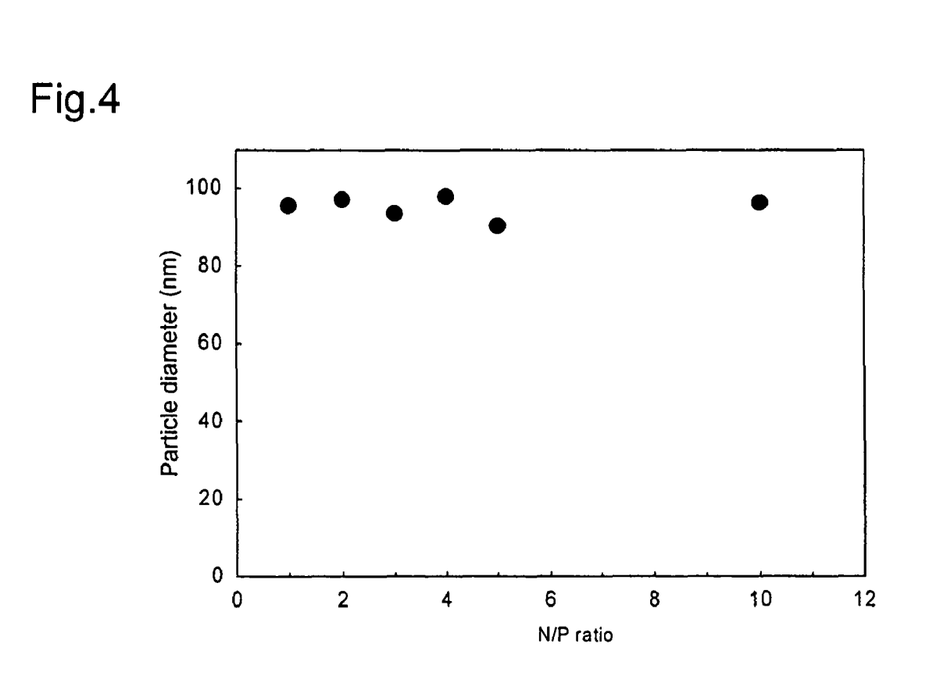
FIG. 4 is a graph showing the measured result of N/P ratio dependency of particle diameter of associated particles formed of MeO-PEG-MOPA and p-DNA.
Figure 5:
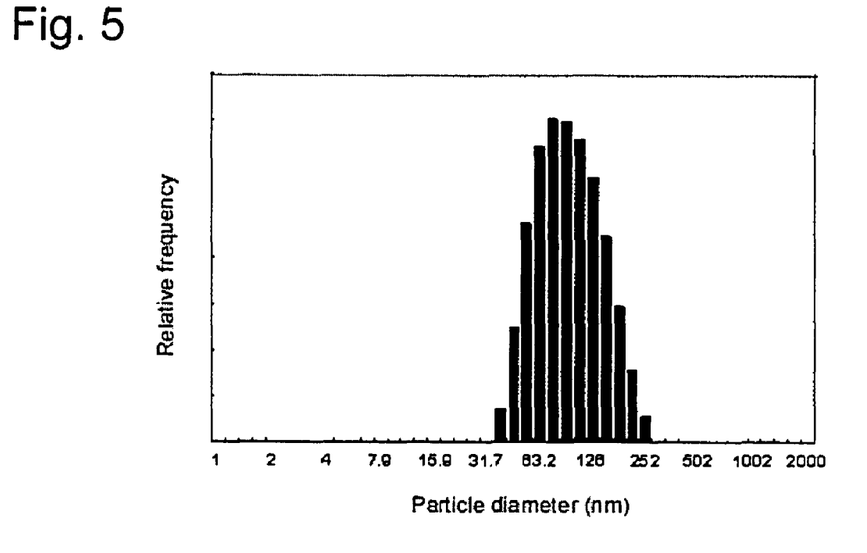
FIG. 5 is a graph showing particle size distribution of associated particles formed of MeO-PEG-DET and p-DNA, as measured by means of dynamic light scatting (DLS).
Figure 6:
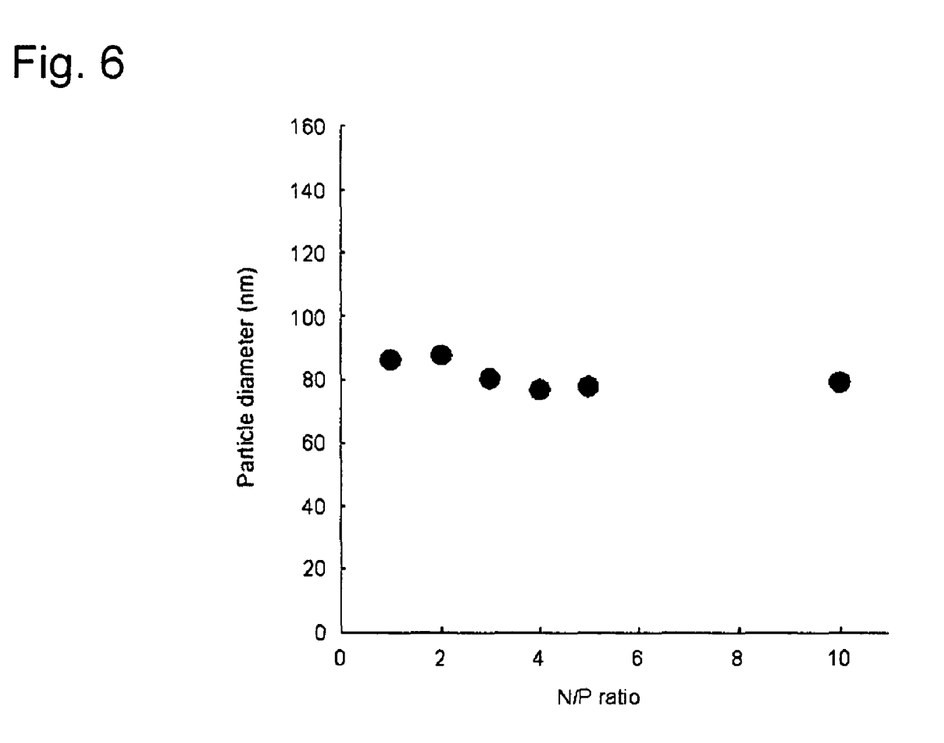
FIG. 6 is a graph showing the measured result of N/P ratio dependency of particle diameter of associated particles formed of MeO-PEG-DET and p-DNA.

3-6. FIGS. 3 and 4 show the results with MeO-PEG-MOPA and p-DNA mixed solutions and FIGS. 5 and 6, those with MeO-PEG-DET and p-DNA mixed solutions. FIGS. 3 and 5 show the particle size distribution at N/P ratio of 1, and FIGS. 4 and 6 show the results of the measurements at various N/P ratios. These results demonstrate formation of single-peak distribution of associated particles having the particle sizes ranging 80-100 nanometers in both systems, and it can be understood they have approximately constant particle size irrelevant to the N/P ratio.

EXAMPLE 7

Characterization by Zeta Potential Measurement

Figure 7:
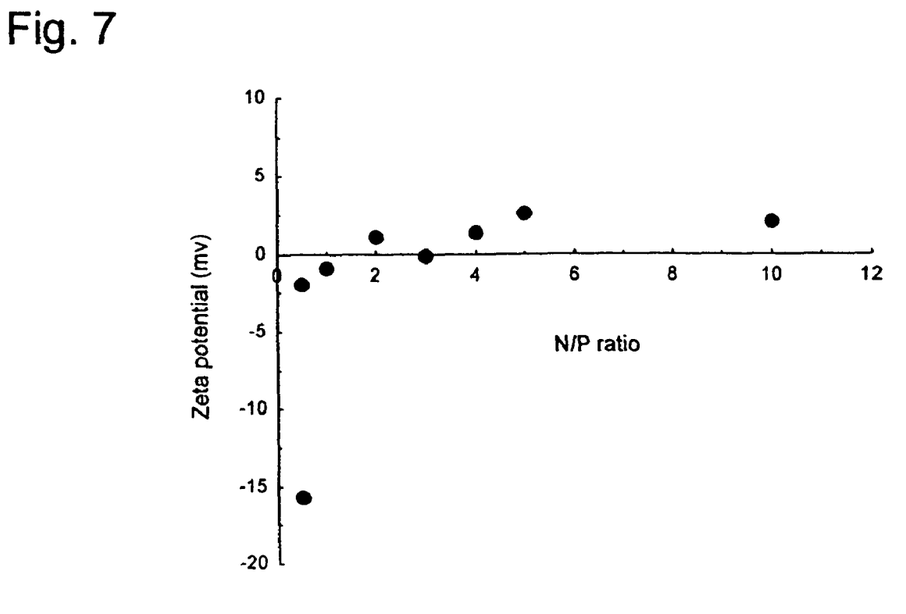
FIG. 7 is a graph showing the zeta potential measurement result of associated particles formed of MeO-PEG-MOPA and p-DNA.
Figure 8:
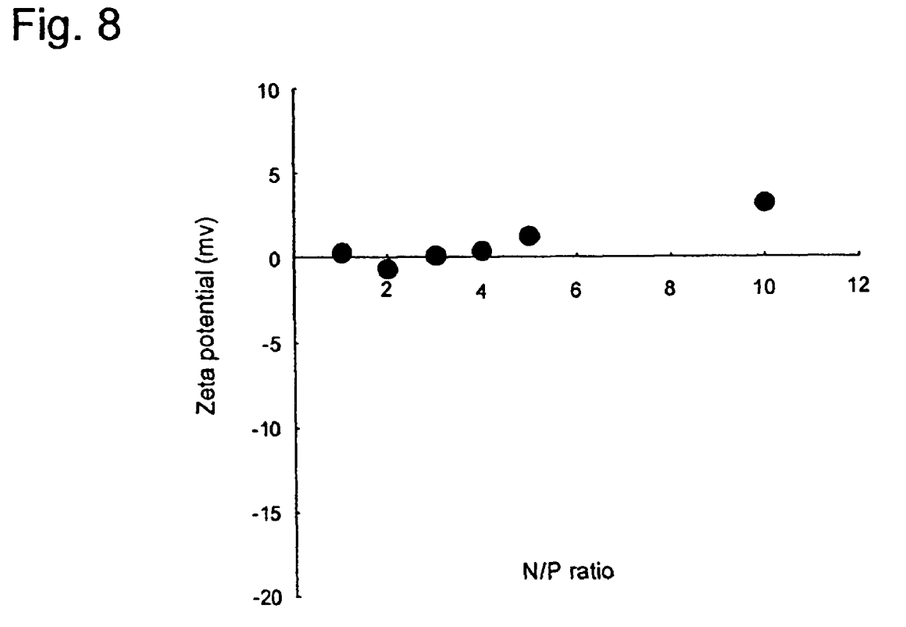
FIG. 8 is a graph showing the zeta potential measurement result of associated particles formed of MeO-PEG-DET and p-DNA.

The results of zeta potential measurements are shown in FIGS. 7 and 8. FIG. 7 shows the result with MeO-PEG-MOPA and p-DNA mixed solutions and FIG. 8 shows those of MeO-PEG-DET and p-DNA mixed solutions. In both systems a minor tendency for positive charging with rise in N/P ratio was observed but the absolute values were very small, and showed zeta potentials close to 0 mV.

This signifies that surfaces of formed associated particles are electrically close to neutral, suggesting a core-shell type structure having a PEG layer at the surface and polyion complex at the inner core.

EXAMPLE 8

Characterization by Ethidium Bromide Assay

Degree of condensation of p-DNAs inside the PIC micelles was evaluated by ethidium bromide assay. The fluorescence intensity of 590 nm reflects the degree of condensation of p-DNAs inside the micelles. That is, higher fluorescence intensity signifies that p-DNAs are in more relaxed (free) state, and lower fluorescence intensity, more condensed state of the p-DNAs. In plotting, the fluorescence intensity of 590 nm measured upon addition of ethidium bromide to p-DNA at a prescribed concentration was standardized as 100, and the measured values were plotted as relative intensities thereto.

Figure 9:
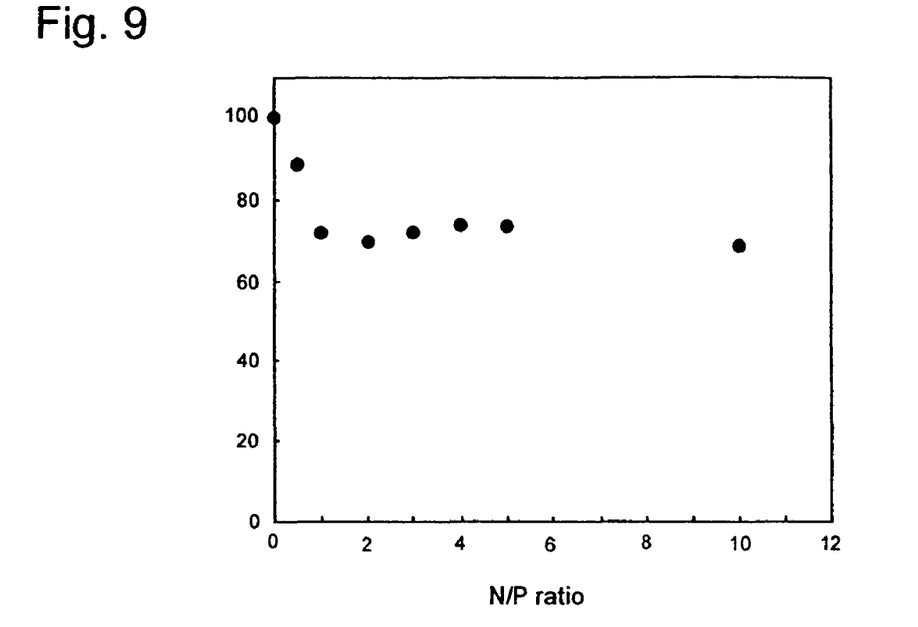
FIG. 9 is a graph showing the result of ethidium bromide assay (10 mM Tris-HCl buffer, pH=7.4) of associated particles formed of MeO-PEG-MOPA and p-DNA.

The measured results with the micelles formed of MeO-PEG-MOPA and p-DNAs were as shown in FIG. 9. With rise in the N/P ratio, the fluorescence intensity showed a tendency for minor decrease, but even at the N/P ratio of 10, the intensity was still about 70. Compared with block copolymers which have been studied in the past, this value is very high (where a polycation which effectively condenses DNAs such as polylysine is used, the relative fluorescence intensity decreases to about 5 at N/P>1).

Figure 10:
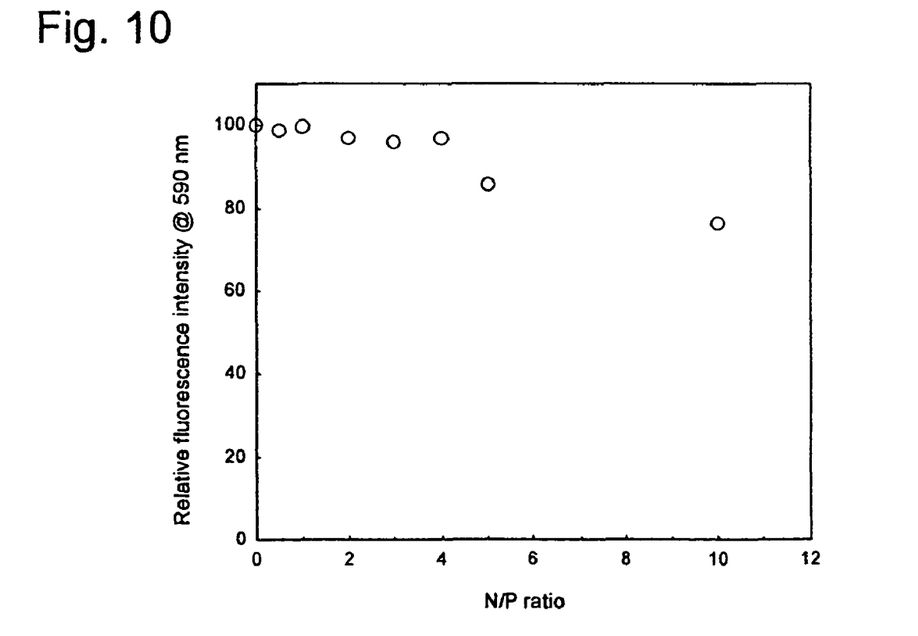
FIG. 10 is a graph showing the result of ethidium bromide assay (10 mM Tris-HCl buffer+150 mM NaCL, pH=7.4) of associated particles formed of MeO-PEG-MOPA and p-DNA under physiological saline concentration condition.

Also the results of similar measurements of a system to which table salt was added at a physiological concentration (150 mM) were as shown in FIG. 10. The relative fluorescence intensity further approached to 100, indicating that the p-DNAs in the micelles were in a relaxed state at about the same level with free p-DNAs. In actual administration of micelles to cutured cells or living bodies, the state as illustrated in FIG. 10 is considered closer to the real conditions, rather than that as illustrated in FIG. 9.

Figure 11:
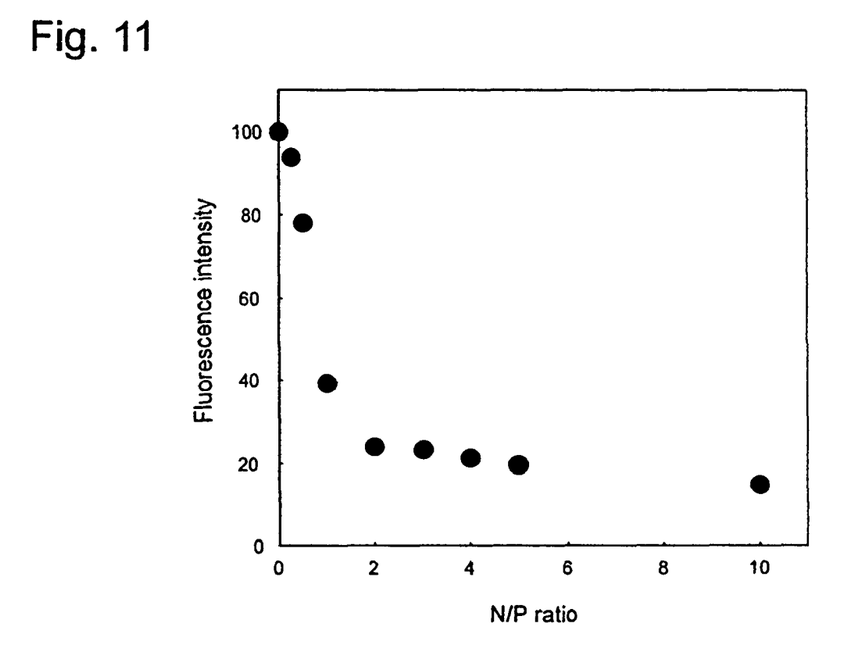
FIG. 11 is a graph showing the result of ethidium bromide assay (10 mM Tris-HCl buffer, pH=7.4) of associated particles formed of MeO-PEG-DET and p-DNA.

The results of the measurements of the micelles formed of MeO-PEG-DET and p-DNAs were as shown in FIG. 11. Within the N/P ratio range of 0-2, rapid decrease in the fluorescence intensity was observed with the rise in the N/P ratio, and during the N/P ratio increase from 2 to 10, gentle decrease in the fluorescence intensity was observed.

EXAMPLE 9

Evaluation of Gene Transfer Effectivity

Figure 12:
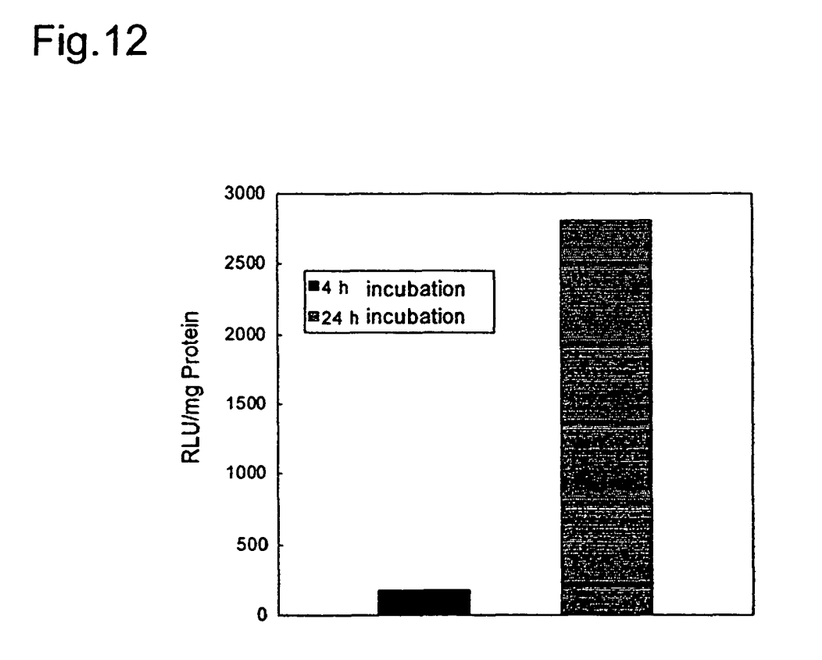
FIG. 12 is a graph showing gene transfer effectivity from associated micelles formed of MeO-PEG-MOPA and p-DNA (N/P=5) into 293 T-cells (by 4 hours' and 24 hours' incubation, respectively).

A micelle of MeO-PEG-MOPA and p-DNA was prepared at N/P=5, which was contacted with cultured cells (293 T cells) for a fixed time and thereafter the culture medium was replaced with a new one. Continuing the incubation for further 24 hours, the gene transfer effectivity was evaluated by luciferase assay, and quantitation of proteins. The results were as shown in FIG. 12. When the case of 4 hours' contact of the micelle with the cells is compared with that of 24 hours' contact, it can be understood that the extension of the contact time drastically improved the gene transfer effectivity. This is presumed to be caused by the change in release rate of the genes enclosed in the micelle.

Figure 13:
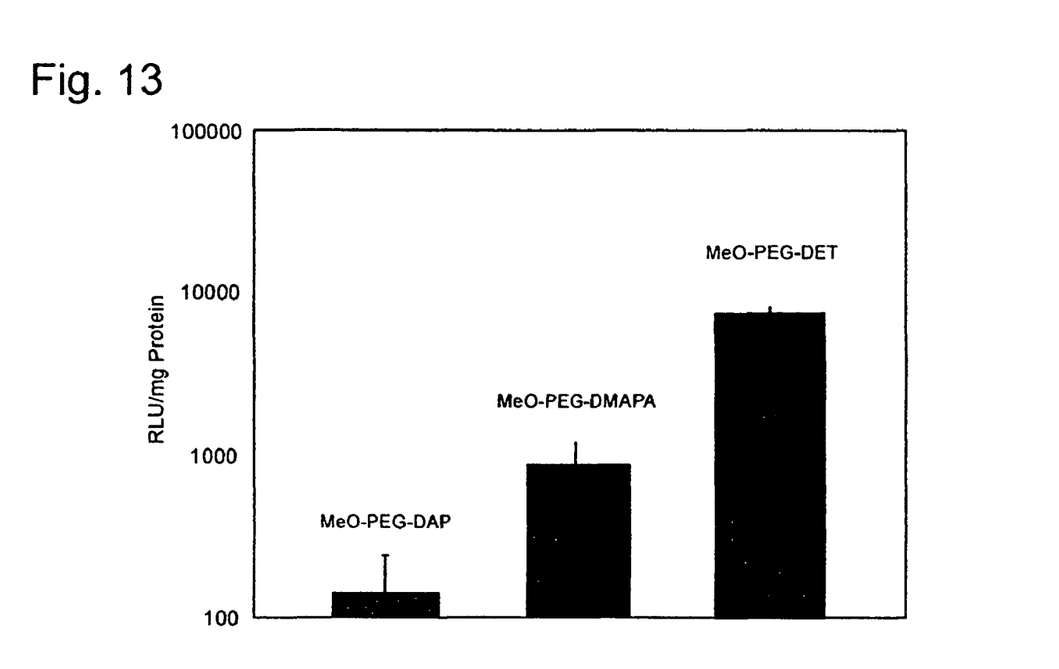
FIG. 13 is a graph showing gene transfer effectivity from associated micelles formed of MeO-PEG-DET, MeO-PEG-DMAPA or MeO-PEG-DAP and p-DNA (N/P=10) into 293 T cells (by 24 hours' incubation).

As for MeO-PEG-DET, those MeO-PEG-DMAPA and MeO-PEG-DAP as prepared in Comparative Examples 1 and 2 were used as the control samples for evaluation. MeO-PEG-DET had both primary amine and secondary amine at the same time; MeO-PEG-DMAPA had tertiary amine only; and MeO-PEG-DAP had primary amine only. Micelles of the three kinds of copolymers each with p-DNAs were prepared at N/P=10, which were contacted with cultured cells (293 T cells) for 24 hours and the culture medium was renewed. After further 24 hours' incubation, gene expression effectivity was evaluated by means of luciferase assay and quantitation of proteins. The results were as shown in FIG. 13. MeO-PEG-DET exhibited higher gene transfer effectivity than the other two kinds of copolymers. This is considered to be caused by the introduction of the amine (primary) participating in the complex formation and the amine (secondary), which is expected to exhibit buffer ability, into one copolymer, whereby the transfer of p-DNAs enclosed in the PIC micelles taken into the cells is promoted by the proton sponge effect.

INDUSTRIAL UTILIZABILITY

According to the present invention, PIC micelles having high gene transfer effectivity can be provided. The present invention also enables provision of more useful non-viral gene vectors. Therefore, the present invention is useful for medical industries.

The invention claimed is:

1. A polyethylene glycol/polycation block copolymer represented by formula (II) or a salt thereof, (II)

in which $R^1$ stands for hydrogen, or a substituted or unsubstituted, straight or branched chain $C_{1-12}$ alkyl, $L^2$ stands for a linker, $R^2$ stands for methylene or ethylene, $R^4$ is either the same as $R^5$ or the formula —NH—$R^9$, wherein $R^9$ is unsubstituted or substituted straight or branched chain $C_{1-20}$ alkyl, $R^5$s each independently stands for hydroxyl, oxybenzyl or —NH—$(CH_2)_a$—X group, wherein X each independently stands for an amine containing one, two or more members of the group consisting of primary, secondary and tertiary amines and quaternary ammonium salt, with the proviso that at least 85% of $R^5$s are —NH—$(CH_2)_a$—X, a is an integer of 1-5, m is an integer of 5-20,000, n is an integer of 2-5,000 and x is an integer of 0-5,000, with a proviso that x is not greater than n.

2. A copolymer as set forth in claim 1, in which the structure of the block copolymer is one represented by a general formula (IV) or a salt thereof, $$R^1O-(CH_2CH_2O)_m-L^2-(NHCHCO)_{n-y-z}-(NHCHR_2CO)_y-(NHCHCO)_z-R^4 \quad (IV)$$
$$\begin{array}{ccc} | & | & | \\ R^2 & C{=}O & (CH_2)_4 \\ | & | & | \\ C{=}O & R^5 & NHR^6 \\ | & & \\ R^5 & & \end{array}$$

in which
- $R^1$ stands for hydrogen, or a substituted or unsubstituted, straight or branched chain $C_{1-12}$ alkyl,
- $L^2$ stands for a linker,
- $R^2$ stands for methylene or ethylene,
- $R^4$ is either the same as $R^5$ or the formula —NH—$R^9$, $R^9$ being unsubstituted or substituted, straight or branched chain $C_{1-20}$ alkyl,
- $R^5$s each independently stands for hydroxyl, oxybenzyl or —NH—$(CH_2)_a$—X group, wherein X each independently stands for an amine containing one, two or more members of the group consisting of primary, secondary and tertiary amines and quaternary ammonium salt,
- a is an integer of 1-5,
- $R^6$ each independently stands for hydrogen or a protective group, wherein the protective group is Z, Boc, acetyl, trifluoroacetyl or the like which are customarily used as protective groups of amino,
- m is an integer of 5-20,000,
- n is an integer 2-5,000,
- y is an integer of 0-4,999 and
- z is an integer of 1-4,999, with the proviso that z is less than n and y+z is not more than n, in the above formulae,
- $X^3$ stands for amino $C_{1-6}$ alkyl,
- $R^7$ stands for hydrogen or methyl,
- d stands for an integer of 1-5,
- e stands for an integer of 1-5,
- f stands for an integer of 0-15, and
- $R^8$ stands for a protective group, wherein the protective group is carboxybenzyl, Boc, acetyl or trifluoroacetyl which are customarily used as protective groups of amino.

3. A copolymer as set forth in claim 1, in which $R^1$ is methyl.

4. A copolymer as set forth in claim 1, in which $R^1$ stands for substituted straight or branched chain $C_{1-12}$ alkyl, wherein the substituent is acetalized formyl, cyano, formyl, carboxyl, amino, $C_{1-6}$ alkoxycarbonyl, $C_{2-7}$ acylamide, same or different tri-$C_{1-6}$ alkylsiloxy, siloxy or silylamino.

5. A copolymer as set forth in claim 1, in which $L^2$ is —$(CH_2)_c$—CO—, c being an integer of 1-5.

6. A copolymer as set forth in claim 1, in which $R^2$ is methylene.

7. A copolymer as set forth in claim 1, in which X is selected from the group consisting of the following Groups B, C, and D:

Group B:

[piperazine structure with N-$X^3$]   or   —(NR$^7$(CH$_2$)$_d$)$_e$—NH$_2$

Group C:
—$(CH_2)_f$—NH$_2$

Group D:
—(NR$^7$(CH$_2$)$_d$)$_e$—NHR$^8$, —N(CH$_3$)$_2$ or —N(CH$_2$CH$_3$)$_2$ 8. A copolymer as set forth in claim 1, in which $R^4$ is —NH—$R^9$, $R^9$ standing for unsubstituted or substituted, straight or branched chain $C_{1-20}$ alkyl.

9. A polyion complex comprising a copolymer as described in claim 1 and nucleic acid or anionic protein.

10. A polyion complex as described in claim 9, which is in the form of a polymer micelle carrying nucleic acid or anionic protein in its core portion with the shell portion composed mainly of the polyethylene glycol segment.

* * * * *